United States Patent
De Barochez et al.

[11] Patent Number: 5,980,952
[45] Date of Patent: Nov. 9, 1999

[54] PHARMACEUTICAL COMPOSITION FOR THE PROGRAMMED RELEASE OF DEXFENFLURAMINE

[75] Inventors: Bruno Huet De Barochez, Ingre; Claude Dauphant, Olivet; Patrick Wuthrich, Orleans, all of France

[73] Assignee: Adir Et Compagnie, Courbevoie, France

[*] Notice: This patent issued on a continued prosecution application filed under 37 CFR 1.53(d), and is subject to the twenty year patent term provisions of 35 U.S.C. 154(a)(2).

[21] Appl. No.: 09/024,364

[22] Filed: Feb. 17, 1998

[30] Foreign Application Priority Data

Feb. 28, 1997 [FR] France ................................. 97 02446

[51] Int. Cl.[6] ............................. A61K 9/50; A61K 31/135
[52] U.S. Cl. ...................... 424/495; 424/497; 424/490; 424/489; 514/909; 514/910
[58] Field of Search .................... 424/490, 497, 424/489, 495; 514/909, 910

[56] References Cited

U.S. PATENT DOCUMENTS

| | | |
|---|---|---|
| 2,738,303 | 3/1956 | Blythe . |
| 4,309,445 | 1/1982 | Wurtman et al. . |
| 4,452,815 | 6/1984 | Wurtman et al. . |
| 4,649,161 | 3/1987 | Wurtman et al. . |
| 4,728,512 | 3/1988 | Mehta et al. . |
| 4,728,513 | 3/1988 | Ventouras . |
| 5,084,287 | 1/1992 | Gherbre-Sellassie . |
| 5,213,811 | 5/1993 | Frisbee et al. . |
| 5,258,186 | 11/1993 | Ohmura et al. . |
| 5,334,392 | 8/1994 | Cuine et al. . |
| 5,445,829 | 8/1995 | Paradissis et al. . |
| 5,502,080 | 3/1996 | Hitzig . |
| 5,547,683 | 8/1996 | Yano et al. . |

FOREIGN PATENT DOCUMENTS

| | | |
|---|---|---|
| 2663539 | 10/1994 | France . |
| 98/37876 | 9/1998 | WIPO . |

OTHER PUBLICATIONS

Merck Index, Eleventh Edition, p. 674, No. 4015.
Aronne, Modern Medical management of Obesity: The Role of Pharmaceutical Intervention, J. Am. Diet. Assoc. 98(10 Suppl. 2), S23–S26, 1998.

*Primary Examiner*—Thurman K. Page
*Assistant Examiner*—Brian K. Seidlech
*Attorney, Agent, or Firm*—The Firm of Gordon W. Hueschen

[57] ABSTRACT

A novel pharmaceutical composition allowing the programmed release of dexfenfluramine containing a water-soluble acid addition salt of dexfenfluramine on a mixture of minigranules, both rapid release and slow release minigranules, permits the attainment of two concentration peaks in the plasma of patients treated therewith.

9 Claims, 6 Drawing Sheets

PHARMACEUTICAL COMPOSITION FOR THE PROGRAMMED RELEASE OF DEXFENFLURAMINE

FIELD OF THE INVENTION

The present invention relates to a pharmaceutical composition for the programmed release of dexfenfluramine via the oral route.

BACKGROUND OF THE INVENTION AND PRIOR ART

Dexfenfluramine is the dextro isomer of fenfluramine and is an active principle used widely in the treatment of obesity.

At the present time, this active principle is administered orally, twice a day, in the form of an immediate-release gelatin capsule containing a 15 mg dose of dexfenfluramine hydrochloride. United States patents relating to fenfluramine, its isomers, and acid addition salts thereof include the following: 3,198,833, 3,198,834, 4,309,445, 4,452,815, 4,649,161, and 5,502,080. Fenfluramine is item 4015 on page 674 of The Merck Index, Twelfth Edition.

OBJECTS OF THE INVENTION

It is an object of the present invention to provide a pharmaceutical composition for the programmed release of dexfenfluramine which contains rapid-release minigranules and slow-release minigranules, both containing a dexfenfluramine pharmaceutically-acceptable acid addition salt, preferably the hydrochloride; such a composition wherein the rapid-release minigranules consist of neutral supports upon which the dexfenfluramine pharmaceutically-acceptable acid addition salt is deposited, and wherein the slow-release minigranules consist of neutral supports upon which dexfenfluramine pharmaceutically-acceptable acid addition salt and talc are deposited, the latter being coated with a polymer which allows the controlled release of active principle and with a surfactant; such a pharmaceutical composition whereby, upon ingestion by a human, two concentration peaks of dexfenfluramine are obtained in the plasma which are spaced out over a period of time; and such a pharmaceutical composition which is particularly useful in the treatment of obesity. Other objects of the invention will be apparent to one skilled in the art, and still additional objects of the invention will become apparent hereinafter.

SUMMARY OF THE INVENTION

What we believe to be our invention, then, inter alia, comprises the following, singly or in combination:

A pharmaceutical composition for the programmed release of dexfenfluramine, which contains rapid-release minigranules and slow-release minigranules, both comprising a dexfenfluramine pharmaceutically-acceptable acid addition salt; such a pharmaceutical composition wherein the rapid-release minigranules consist of neutral supports upon which the dexfenfluramine pharmaceutically-acceptable acid addition salt is deposited, and the slow-release minigranules consist of neutral supports upon which dexfenfluramine pharmaceutically-acceptable acid addition salt and talc are deposited and which are coated with a polymer which allows the controlled release of active principle and with a surfactant; such a pharmaceutical composition wherein the rapid-release minigranules are coated with a polymer which allows rapid release of the active principle; such a pharmaceutical composition wherein the polymer coating the slow-release minigranules is a cellulose derivative or a copolyacrylic derivative; such a pharmaceutical composition wherein the polymer is ethylcellulose; such a pharmaceutical composition wherein the surfactant coating the slow-release minigranules is a salt of a fatty alcohol ester or a polysorbate; such a pharmaceutical composition wherein the sodium salt of a fatty alcohol ester is sodium lauryl sulfate; such a pharmaceutical composition wherein the slow-release minigranule coating contains a plasticizer; such a pharmaceutical composition wherein the plasticizer is acetyl tributyl citrate; such a pharmaceutical composition wherein the slow-release minigranules contain a stabilizer in their coating; such a pharmaceutical composition wherein the stabilizer is cetyl alcohol; such a pharmaceutical composition wherein the neutral supports are neutral sucrose starch microgranules; such a pharmaceutical composition wherein the composition is in the form of a gelatin capsule; such a pharmaceutical composition wherein the active-ingredient comprising minigranules are manufactured by mounting, after which a coating operation is or is not carried out; such a pharmaceutical composition whereby, upon ingestion by a human, two concentration peaks of dexfenfluramine are obtained in the human plasma, which are spaced out over time; such a pharmaceutical composition wherein:
the rapid minigranules contain between 10 and 80% dexfenfluramine pharmaceutically-acceptable acid addition salt,
the slow minigranules contain between 10 and 80% dexfenfluramine pharmaceutically-acceptable acid addition salt,
the percentage of talc contained in the slow-release minigranules is between 10 and 80% of the mass of active principle,
the percentage of surfactant contained in the slow-release minigranules is between 0.05 and 3% of the total mass of the minigranules before coating, and
the percentage of the polymer used for coating of the slow-release minigranules is between 3 and 20% of the total mass of the minigranules before coating; such a pharmaceutical composition wherein the dexfenfluramine pharmaceutically-acceptable acid addition salt is dexfenfluramine hydrochloride; such a pharmaceutical composition wherein:
the rapid minigranules contain between 10 and 80% dexfenfluramine hydrochloride,
the slow minigranules contain between 10 and 80% dexfenfluramine hydrochloride,
the percentage of talc contained in the slow-release minigranules is between 10 and 80% of the mass of active principle,
the percentage of surfactant contained in the slow-release minigranules is between 0.05 and 3% of the total mass of the minigranules before coating, and
the percentage of the polymer used for coating of the slow-release minigranules is between 3 and 20% of the total mass of the minigranules before coating; and such a pharmaceutical composition which is useful in the treatment of obesity.

GENERAL DESCRIPTION OF THE INVENTION

The Applicant has now developed a sustained-release form of dexfenfluramine which has the advantage for the patient of being administered only once a day.

Moreover, whereas most sustained-release forms make it possible only to sustain the release of the active principle over time, the novel pharmaceutical composition which is the subject of the present invention has the advantage not only of sustaining the release of the active principle but also of delaying this release. This makes it possible to modify the release of the active principle as a function of the time of the day and thus to obtain in the plasma two concentration peaks which, as a function of the percentage of the constituents of this pharmaceutical composition, may be adapted to the requirements of the treatment.

Lastly, this novel pharmaceutical form is entirely suited to the physicochemical characteristics of dexfenfluramine.

In this novel pharmaceutical form, the active principle is administered chronobiologically: a first part of the active principle is released instantaneously, the other part is released after a few hours, thereby making it possible to obtain in the plasma two concentration peaks which are spaced out over time.

BRIEF DESCRIPTION OF THE DRAWINGS

Reference is now made to the drawings for a better understanding of the invention and in which.

MORE SPECIFIC DESCRIPTION OF THE INVENTION

The pharmaceutical composition according to the invention consists of:

rapid-release minigranules, slow-release minigranules.

These minigranules are then together placed in a pharmaceutically-acceptable form.

These pharmaceutically acceptable forms are preferably gelatin capsules or tablets.

The rapid-release minigranules consist of neutral supports on which the active principle is deposited. These minigranules may optionally be coated with a polymer which allows rapid release of the active principle.

The slow-release minigranules consist of neutral supports on which the active principle and talc are deposited. These minigranules are then coated with a polymer which allows control of the release of the active principle, and with a surfactant. This coating may also contain other excipients such as plasticizers or stabilizers.

The neutral supports used in the minigranules are more particularly neutral microgranules and preferably sucrose-starch microgranules.

Other materials which may be employed as neutral support include neutral minigranules of lactose, sucrose, a mixture of sugar other than sucrose and starch, and microcrystalline cellulose.

In order better to fix the active principle to these neutral supports, various binders may be used such as, for example, methylhydroxypropylcellulose.

Other materials besides methylhydroxypropylcellulose which can be employed as binder include povidone, hydroxyethylcellulose, hydroxypropylcellulose, non-cellulosic materials such as maltodextrine, and amidon (maize, corn, potato, or rice starch).

Among the polymers optionally used to coat the rapid-release minigranules, mention may be made of cellulose polymers allowing rapid release of the active principle. The preferred polymer is a methylhydroxypropylcellulose of low viscosity.

Other cellulose polymers which may be used include hydroxyethylcellulose, hydroxypropylcellulose, methylcellulose, methylhydroxyethylcellulose, and methylethylcellulose, whereas other polymers of a non-cellulosic nature which may be employed are povidone (polyvinylpyrrolidone) and maltodextrines.

Among the polymers used for coating of the slow-release minigranules, mention may be made of water-insoluble cellulose derivatives such as, for example, ethylcellulose and cellulose acetate and acrylic copolymers. The preferred polymer is ethylcellulose.

Other non-cellulosic insoluble polymers which may be employed include copolymers of methacrylic acid and methylmethacrylate and copolymers of methacrylic acid and ethylacrylate, which may be utilized in a suitable organic solution or in the form of an aqueous dispersion. Another type of water-insoluble polymer which may be employed includes various water-insoluble silicones.

Among the surfactants used for coating of the slow-release minigranules, mention may be made of salts of fatty alcohol esters or polysorbates. The preferred surfactant is sodium lauryl sulfate.

The surfactant employed is preferably a GRAS surfactant and, among others which may be employed, are included sodium dodecylsulfate, and Polysorbate 20, 60, and 80.

Among the plasticizers optionally used for coating of the slow-release minigranules, mention may be made of citric acid esters and sebacates. The preferred plasticizer is acetyl tributyl citrate.

Additional plasticizers which may be employed include triethyl citrate, tributyl citrate, acetyl triethyl citrate, dibutyl sebacate, diethyl phthalate, and dibutyl phthalate.

Among the stabilizers which may also be employed in the coating for the slow-release minigranules, mention may preferably be made of cetyl alcohol.

Lastly, these two types of minigranules may also contain conventionally used excipients such as dyes, flavorings, fillers, etc. and may contain anticaking agents which prevent the minigranules from sticking together during their preparation.

The slow or rapid minigranules are manufactured either by extrusion and spheronization which may or may not be followed by a coating operation, or by mounting and coating. The preferred process for manufacturing these minigranules is mounting followed by coating.

The rapid minigranules are prepared by mounting, that is to say by spraying an aqueous solution of the active principle which may contain a binder, for example methylhydroxypropylcellulose, onto a neutral support, for example neutral sucrose-starch microgranules. The minigranules are dried as the mounting proceeds, either using a granulating or film-forming turbomixer provided with a blower and hot-air suction, or using a machine with a fluidized-air bed. Once the active principle has been deposited on the neutral supports, a protective coating is optionally applied, using the same apparatus. The polymer used to protect the minigranules should allow rapid release of the active principle.

The slow minigranules are prepared according to the same mounting principle and also using a binder, talc being added to the mounting solution. The coating of these minigranules is applied using the same coating procedure and apparatus.

The definition of "talc" as used herein is according to the European Pharmacopeia, that is, talc is a native hydrous magnesium silicate which sometimes contains variable small proportions of aluminum and iron which are insoluble in dilute sulfuric acid. It is in powdered or pulverulent form, white or nearly white, and practically insoluble in water and also in dilute acid and alkaline solutions. The material is well-known in the art.

It has been shown that the use of talc in the mounting suspension as well as the use of a coating surfactant such as sodium lauryl sulfate makes it possible to obtain delayed release of the active principle. This release may be delayed by four hours or more and modified over time as a function of the percentages of constituents used.

The rapid minigranules contain 10 to 80% dexfenfluramine in the form of a pharmaceutically-acceptable acid addition salt, preferably the hydrochloride. The slow minigranules contain 10 to 80% dexfenfluramine pharmaceutically-acceptable acid addition salt. The percentage of talc deposited upon the slow release minigranules is 10 to 80% of the mass of active principle.

The dexfenfluramine acid addition salt is preferably the hydrochloride, although numerous other pharmaceutically-acceptable acid addition salts are known and may be employed with nearly equal facility. U.S. Pat. Nos. 3,198,833, 3,198,834, 4,309,445, 4,452,815, 4,649,161, and 5,502,080 disclose the hydrochloride and other water-soluble acid addition salts of dexfenfluramine. Representative acid addition salts include the hydrobromide, sulfate, phosphate, nitrate, sulfonate, acetate, succinate, maleate, and tartrate, the selected salt being taken from either inorganic or organic acid addition salts which are water-soluble and many of which are well-known in the art.

The percentage of surfactant coated upon the slow-release minigranules is 0.05% to 3% of the total mass of the minigranules before coating. The percentage of the polymer used for coating of the slow-release minigranules is 3 to 20% of the total mass of the minigranules before coating.

DETAILED DESCRIPTION OF THE INVENTION

The following Examples are given by way of illustration only, and are not to be construed as limiting.

Examples of the Preparation of Delayed- and Sustained-Release Minigranules

EXAMPLE 1

An aqueous suspension of active principle (dexfenfluramine hydrochloride) is sprayed onto neutral sucrosestarch microgranules (Microgranules 710–850 $\mu$m). The suspension contains binder methylhydroxypropylcellulose in a proportion of 2% relative to the amount of active principle, and talc in a proportion of 40% relative to the amount of active principle. The mounting is carried out in a fluidized-air bed. A coating solution containing 5% (m/v) ethylcellulose in ethanol is then sprayed onto the minigranules filled or layered with active principle. This solution contains acetyl tributyl citrate in a proportion of 10% of the mass of ethylcellulose, sodium lauryl sulfate in a proportion of 0.3% (m/v), and stabilizer cetyl alcohol in a proportion of 0.7% (m/v). The coating is carried out in the same machine as used for the mounting operation.

The kinetics of release of the active principle are measured by means of the rotating palette technique described in the European Pharmacopoeia. The flasks are filled with 500 ml of phosphate buffer maintained at 37° C. The paddle speed is 50 rev/min.

Figure 1:
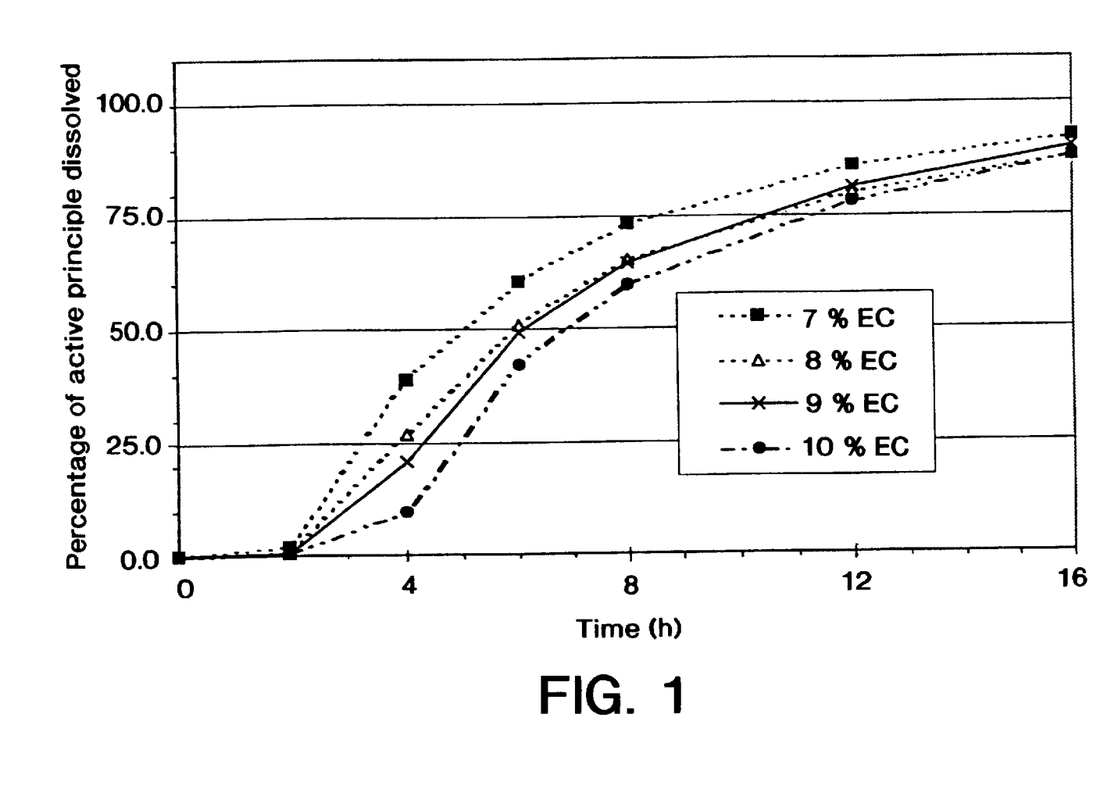
FIG. 1 is a graph showing the release kinetics of compositions according to Example 1 wherein the slow-release microgranules are coated with a coating containing different percentages of ethyl cellulose and showing that the latency time or delay period is dependent upon the concentration of the ethyl cellulose or other coating polymer provided for controlled release of active ingredient.

The coating is carried out so as to obtain a coating containing 7, 8, 9 and 10% ethylcellulose, this percentage being expressed relative to the mass of minigranules mounted. The release kinetics obtained are represented in FIG. 1. A lag time of 2 to 4 hours is observed as a function of the amount of polymer sprayed.

EXAMPLE 2

The minigranules described in this example were prepared according to the process described in Example 1, but contain no talc. The coatings correspond to amounts of ethylcellulose of 9, 12, and 14% ethylcellulose.

Figure 2:
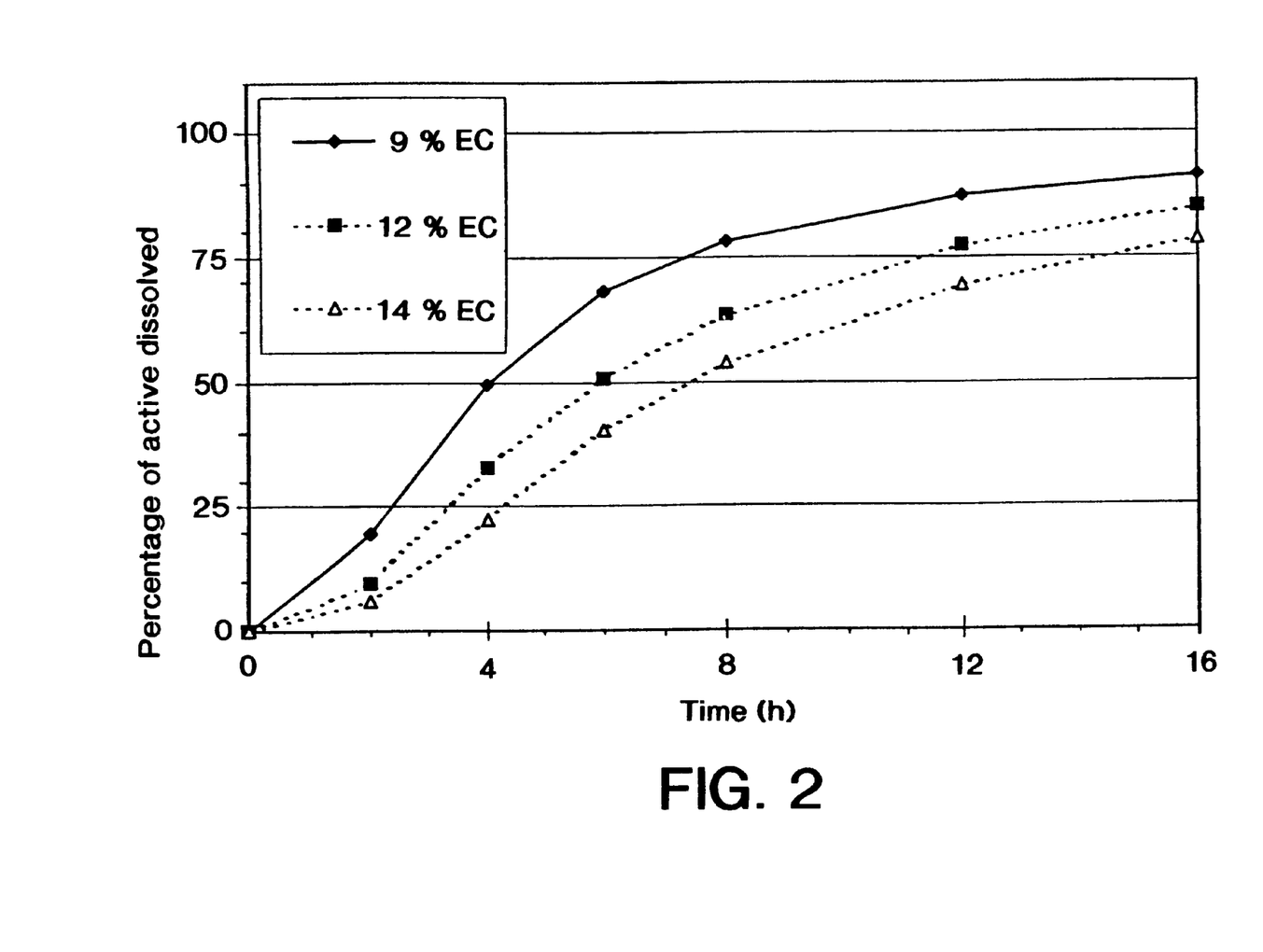
FIG. 2 is a graph showing the release kinetics of slow-release microgranules according to Example 2 containing no talc and varying percentages of ethyl cellulose and demonstrating that a sufficient latency time or delay in release is obtained only when the slow-release minigranules contain talc, as in Example 1.

The release kinetics obtained are represented in FIG. 2.

These curves show clearly that a sufficient lag time can be obtained only when the minigranules contain talc, as in Example 1.

EXAMPLE 3

Figure 3:
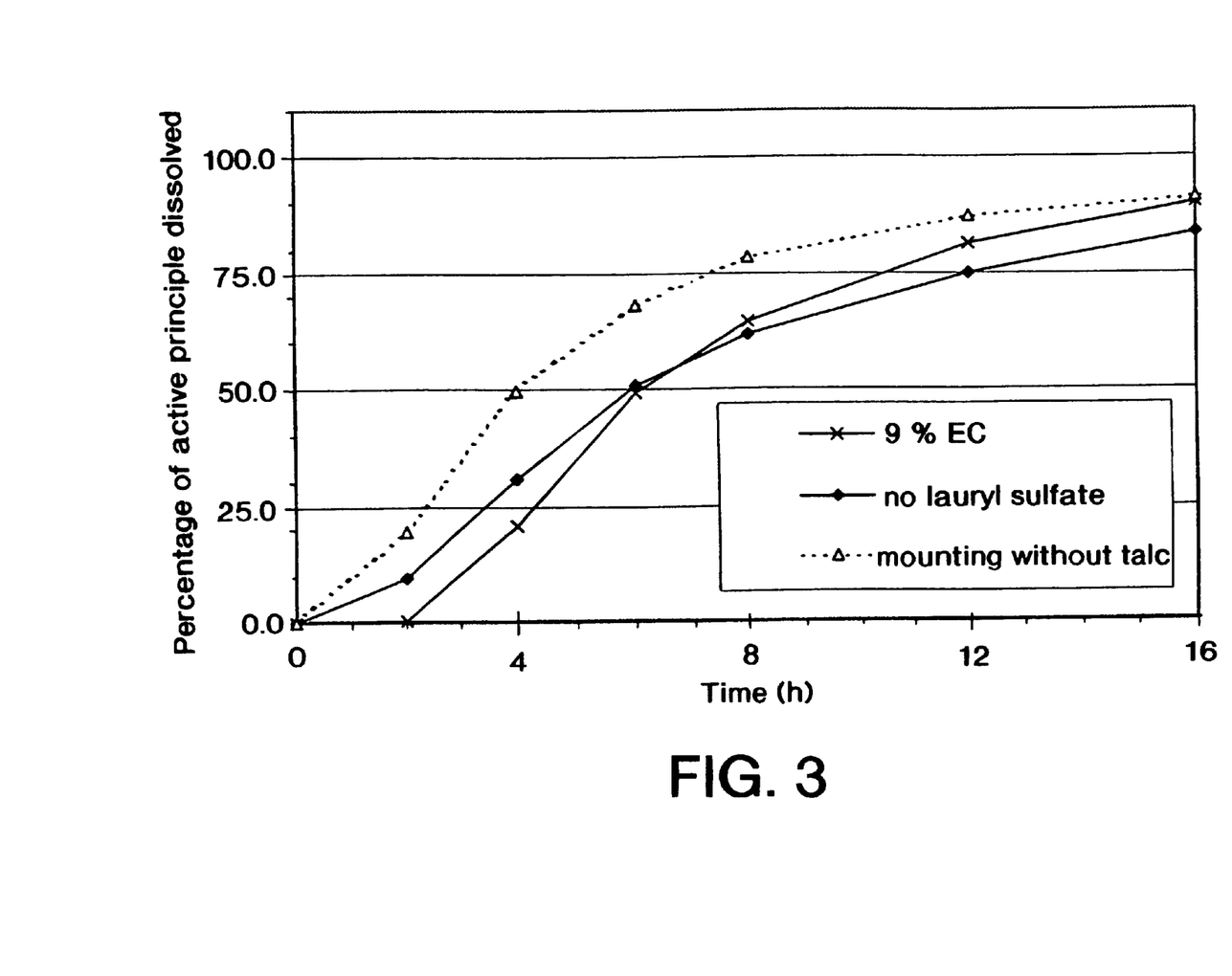
FIG. 3 is a graph showing the release kinetics of a composition according to Example 3 but without surfactant, compared with the release kinetics of the formulation of Example 1 and with the talc-free formula of Example 2, the amount of ethyl cellulose in the coating in each case being 9%, and showing that a combination of talc in the mounting suspension and surfactant in the coating solution are required to obtain a latency time or delay of at least two hours.

Minigranules mounted with talc, identical to those described in Example 1, are coated with an ethylcellulose solution containing acetyl tributyl citrate and no sodium lauryl sulfate. The amount of ethylcellulose sprayed corresponds for each test to 9%. The results are presented in FIG. 3, compared with the corresponding formula of Example 1 and with the corresponding formula of Example 2 (talc-free). It appears that a combination of talc in the mounting suspension and of sodium lauryl sulfate in the coating solution are needed in order to obtain a latency time of at least 2 hours.

Example of the Preparation of Immediate-Release Miniqranules

EXAMPLE 4

An aqueous suspension of active principle (dexfenfluramine hydrochloride) is sprayed on neutral sucrosestarch microgranules. The suspension contains methylhydroxypropylcellulose in a proportion of 2% relative to the amount of active principle. A solution containing 5% (m/v) methylhydroxypropylcellulose in ethanol is then sprayed on the minigranules filled with active principle. The coating is carried out in the same machine as used for the mounting operation.

Examples of Gelatin Capsules Containing Rapid-Release Minigranules and Slow-Release Minigranules

EXAMPLE 5

Formulation A

Formulation A contains two types of minigranules: rapid-release minigranules obtained according to the process described in Example 4. These minigranules are coated using a standard suspension of methylhydroxypropylcellulose containing a red dye. Slow-release minigranules are obtained according to the process described in Example 1 but containing neither talc nor cetyl alcohol nor sodium lauryl sulfate and with an amount of ethylcellulose of 9%. The amounts of these minigranules are such that they make it possible to obtain 10 mg of dexfenfluramine released immediately and 20 mg of dexfenfluramine released in a delayed or sustained manner.

These slow and rapid minigranules are placed in gelatin capsules.

EXAMPLE 6

Formulation B

Formulation B is identical to formulation A but the slow-release minigranules contain talc, cetyl alcohol as stabilizer, and sodium lauryl sulfate.

The unit formulae of formulations A and B are presented in the following table:

| Constituents | Amounts (mg) | | | | |
| --- | --- | --- | --- | --- | --- |
| | Rapid minigranules | Slow minigranules (Formulation A) | Slow minigranules (Formulation B) | Overall formulation A | Overall formulation B |
| Uncoated minigranules | | | | | |
| Dexfenfluramine hydrochloride | 10 | 20 | 20 | 30 | 30 |
| Methylhydroxypropylcellulose | 0.4 | 0.8 | 0.8 | 1.2 | 1.2 |
| Neutral sucrose-starch microgranules | 22.933 | 45.867 | 37.867 | 68.8 | 60.8 |
| Talc | — | — | 8 | — | 8 |
| Rapid-release coating | | | | | |
| Methylhydroxypropylcellulose | 0.8377 | — | — | 0.8377 | 0.8377 |
| Other excipients (dye) | 0.2583 | — | — | 0.2583 | 0.2583 |
| Slow-release coating | | | | | |
| Acetyl tributyl citrate | — | 0.933 | 0.6 | 0.933 | 0.6 |
| Cetyl alcohol | — | — | 0.685 | — | 0.685 |
| Ethylcellulose | — | 9.333 | 6 | 9.333 | 6 |
| Sodium lauryl sulfate | — | — | 0.3 | — | 0.3 |
| Encapsulation with gelatin | | | | | |
| Magnesium stearate | 0.05 | 0.075 | 0.075 | 0.125 | 0.125 |

Figure 4:
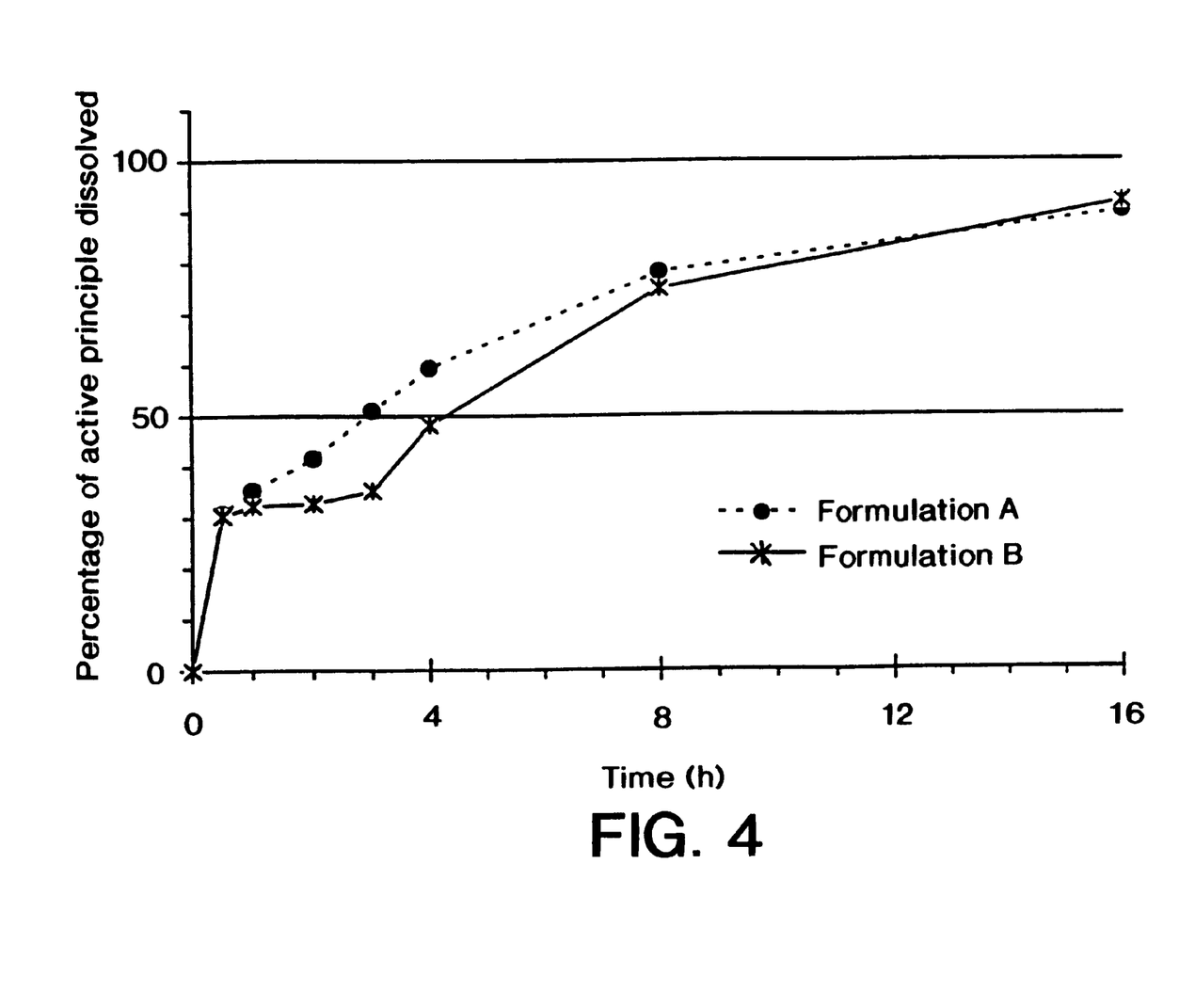
FIG. 4 compares the dissolution kinetics of formulations A and B, formulation B, which contains talc, ethyl alcohol, and surfactant, according to Example 6, exhibiting a latency time or delay of release from the slow-release minigranules, in contrast to the formulation of Example 5, which contains none of these ingredients.

FIG. 4 compares the dissolution kinetics of the two formulations.

A plateau is seen on the profile of formulation B, this plateau corresponding to the latency delay time of the sustained-release minigranules. Formulation A does not exhibit this plateau.

Figure 5:
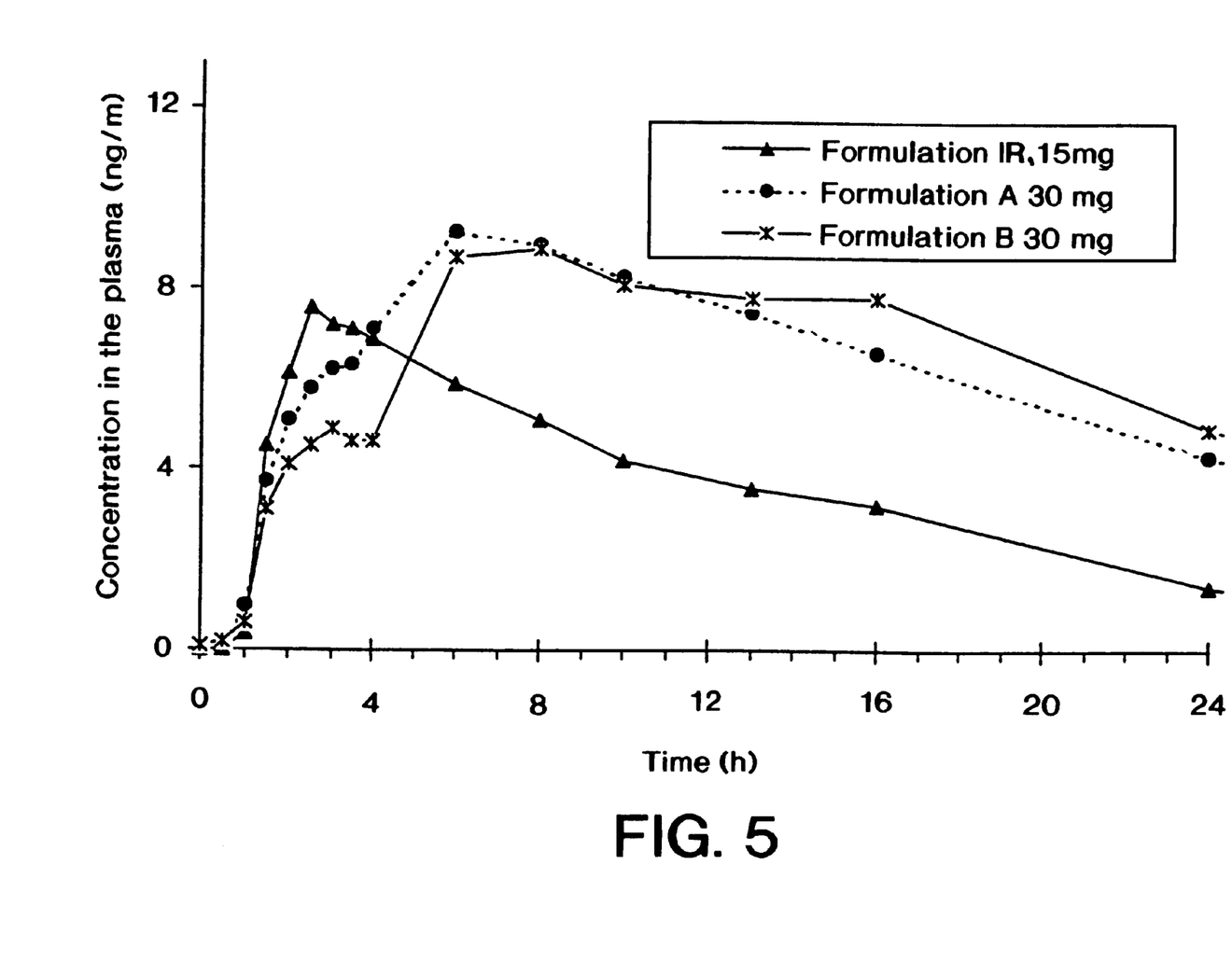
FIG. 5 is a graph showing a mean profile of the plasma concentration of nine healthy volunteers after administration of either an immediate-release formulation (IR) containing a 15 mg dose, or a sustained-release formulation (A) containing a 30 mg dose without any latency time, or a sustained-release formulation (B) containing a 30 mg dose with a 2-hour latency time. The profile of formulation B demonstrates two (2) concentration peaks in the plasma, the first corresponding to the Cmax of the IR formulation at 2.5 to 3-hours and the other concentration peak being approximately eight (8) hours after administration.

These gelatin capsules were used for a pharmacokinetic study, comparing the gelatin capsules of formulations A and B with an immediate-release formulation containing a 15 mg dose of active principle, on 9 healthy male volunteers. The concentrations obtained in the plasma are represented in FIG. 5. The profile of formulation B shows two concentration peaks in the plasma; the first corresponds to the Cmax of the immediate-release form (2.5 to 3 h), the other being at about 8 h.

EXAMPLE 7

Formulation C

Formulation C is identical to formulation B but the immediate-release minigranules are coated using a dye-free suspension of hydroxypropylmethylcellulose. The unit formula of formulation C is presented in the following table:

|  | Amounts (mg) | | |
|---|---|---|---|
| Constituents | Rapid-release minigranules | Slow-release minigranules | Overall formulation |
| Uncoated minigranules | | | |
| Dexfenfluramine hydrochloride | 10 | 20 | 30 |
| Methylhydroxypropylcellulose | 0.4 | 0.8 | 1.2 |
| Neutral sucrose-starch microgranules | 56.267 | 37.867 | 94.134 |
| Talc | — | 8 | 8 |
| Intermediary vehicle, purified water | | | |
| Rapid-release coating | | | |
| Methylhydroxypropylcellulose | 1 | — | 1 |
| Intermediary vehicle, purified water | | | |
| Slow-release coating | | | |
| Acetyl tributyl citrate | — | 0.6 | 0.6 |
| Cetyl alcohol | — | 0.685 | 0.685 |
| Ethylcellulose | — | 6 | 6 |
| Sodium lauryl sulfate | — | 0.3 | 0.3 |
| Intermediary vehicle: ethanol | | | |
| Encapsulation with gelatin | | | |
| Magnesium stearate | 0.075 | 0.075 | 0.15 |
| For an opaque white gelatin capsule filled with | | | 142.069 |

Figure 6:
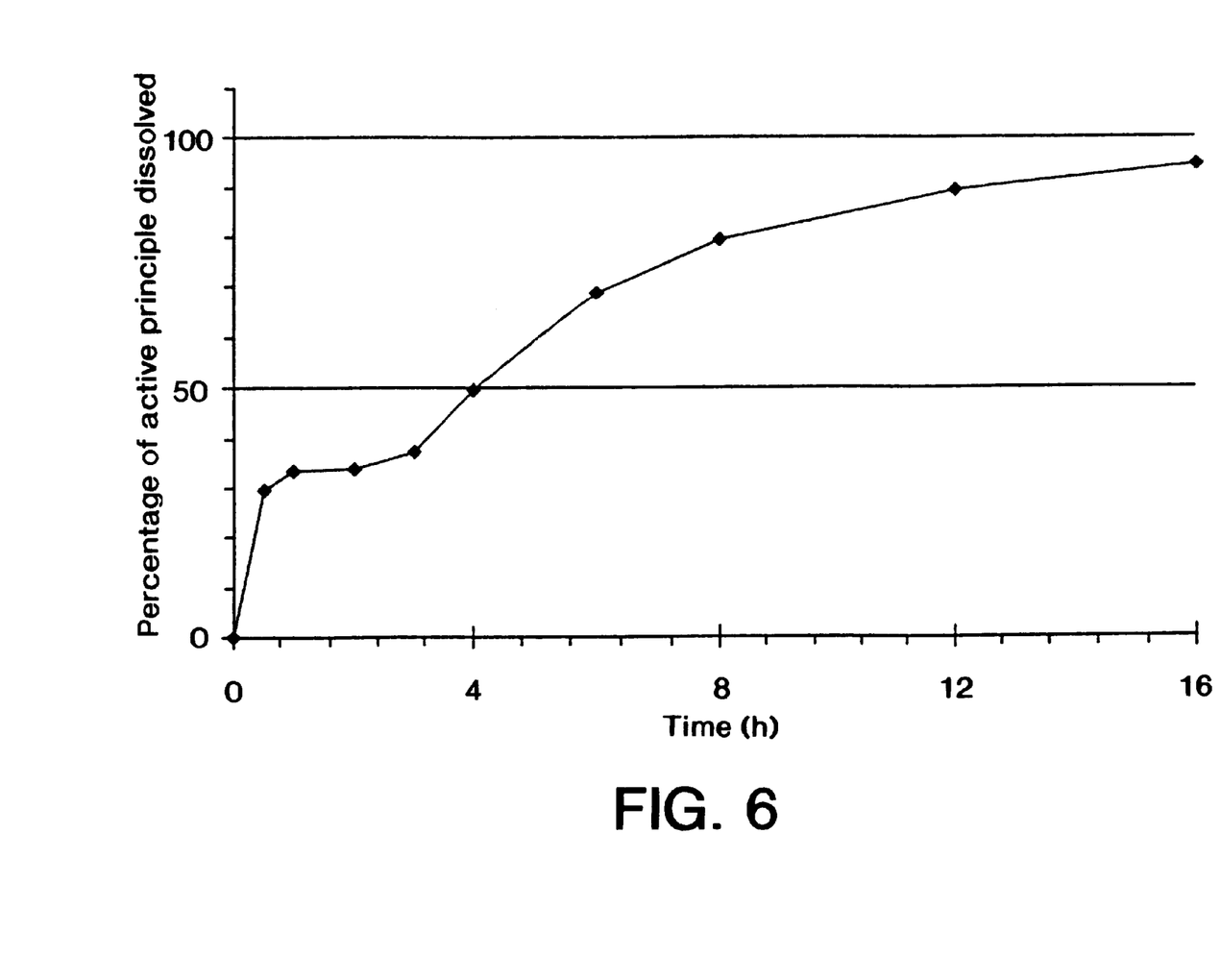
FIG. 6 is a graph showing the in vitro release profile of formulation C, which is identical to formulation B, but wherein the immediate-release minigranules are coated with a dye-free suspension of hydroxypropylmethyl-cellulose according to Example 7. The curve of the graph indicates that the dye suspension has no influence on the release profile of the dexfenfluramine and also demonstrates a sustained-release profile of dexfenfluramine with a steady state during the first four (4) hours of release of active principle.

The in vitro release profile is presented in FIG. 6. It is identical to the profile observed for formulation B: this indicates that the dye suspension used has no influence on the release profile of dexfenfluramine. This curve clearly shows a sustained-release profile of dexfenfluramine, with a steady state obtained during the first four hours of release of the active principle.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

We claim:

1. A pharmaceutical composition for the programmed release of dexfenfluramine, which contains rapid-release minigranules and slow-release minigranules, both comprising a dexfenfluramine pharmaceutically-acceptable acid addition salt, wherein the rapid-release minigranules consist of neutral supports upon which the dexfenfluramine pharmaceutically-acceptable acid addition salt is deposited, and wherein the slow-release minigranules consist of neutral supports upon which the dexfenfluramine pharmaceutically-acceptable acid addition salt and talc are deposited and which are coated with a polymer which allows the controlled release of active principle and with a surfactant, wherein the rapid-release minigranules are coated with methylhydroxypropylcellulose to allow rapid release of the active principle, wherein the polymer coating the slow-release minigranules is ethylcellulose, and wherein the surfactant coating the slow-release minigranules is a salt of a fatty alcohol ester or a polysorbate, wherein the slow-release minigranule coating contains a plasticizer, and wherein the slow-release minigranules contain a stabilizer in their coating.

2. The pharmaceutical composition as claimed in claim 1, wherein the sodium salt of a fatty alcohol ester is sodium lauryl sulfate.

3. The pharmaceutical composition as claimed in claim 1, wherein the plasticizer is acetyl tributyl citrate.

4. The pharmaceutical composition as claimed in claim 1, wherein the stabilizer is cetyl alcohol.

5. The pharmaceutical composition as claimed in claim 1, wherein the neutral supports are neutral sucrose-starch microgranules.

6. The pharmaceutical composition as claimed in claim 1, wherein the composition is in the form of a gelatin capsule.

7. The pharmaceutical composition as claimed in claim 1, wherein:

the rapid minigranules contain between 10 and 80% dexfenfluramine pharmaceutically-acceptable acid addition salt, the slow minigranules contain between 10 and 80% dexfenfluramine pharmaceutically-acceptable acid addition salt, the percentage of talc contained in the slow-release minigranules is between 10 and 80% of the mass of active principle, the percentage of surfactant contained in the slowrelease minigranules is between 0.05 and 3% of the total mass of the minigranules before coating, and the percentage of the polymer used for coating of the slow-release minigranules is between 3 and 20% of the total mass of the minigranules before coating.

8. The pharmaceutical composition as claimed in claim 1, wherein:

the rapid minigranules contain between 10 and 80% dexfenfluramine hydrochloride, the slow minigranules contain between 10 and 80% dexfenfluramine hydrochloride, the percentage of talc contained in the slow-release minigranules is between 10 and 80% of the mass of active principle, the percentage of surfactant contained in the slow-release minigranules is between 0.05 and 3% of the total mass of the minigranules before coating, and the percentage of the polymer used for coating of the slow-release minigranules is between 3 and 20% of the total mass of the minigranules before coating.

9. The pharmaceutical composition as claimed in claim 1, wherein the dexfenfluramine pharmaceutically-acceptable acid addition salt is dexfenfluramine hydrochloride.

* * * * *

UNITED STATES PATENT AND TRADEMARK OFFICE
CERTIFICATE OF CORRECTION

PATENT NO. : 5,980,952
DATED : Nov. 9, 1999
INVENTOR(S) : B.H. De Barochez; C. Dauphant; P. Wuthrich It is certified that error appears in the above-indentified patent and that said Letters Patent is hereby corrected as shown below:

Title Page, Column 2, OTHER PUBLICATIONS, Assistant
    Examiner: "Brian K. Seidlech" should read
    -- Brian K. Seidleck --.

Column 7, line 19: "Miniqranules" should read
    -- minigranules--.

Column 10, line 34: Delete the word "sodium" before
    "salt."

Signed and Sealed this

Twentieth Day of June, 2000

Attest:

Q. TODD DICKINSON

*Attesting Officer*     *Director of Patents and Trademarks*